United States Patent
Giorgetti

(10) Patent No.: US 11,896,569 B2
(45) Date of Patent: *Feb. 13, 2024

(54) COMPOSITIONS COMPRISING AMINO ACIDS FOR USE IN THE TREATMENT OF MUCOSITIDES IN NEOPLASIA PATIENTS UNDERGOING RADIATION THERAPY AND/OR CHEMOTHERAPY

(71) Applicant: Professional Dietetics S.p.A., Milan (IT)

(72) Inventor: Paolo Luca Maria Giorgetti, Milan (IT)

(73) Assignee: Professional Dietetics S.p.A., Milan (IT)

( * ) Notice: Subject to any disclaimer, the term of this patent is extended or adjusted under 35 U.S.C. 154(b) by 33 days.

This patent is subject to a terminal disclaimer.

(21) Appl. No.: 17/515,155

(22) Filed: Oct. 29, 2021

(65) Prior Publication Data

US 2022/0047539 A1  Feb. 17, 2022

Related U.S. Application Data

(63) Continuation of application No. 15/571,130, filed as application No. PCT/IB2016/052724 on May 12, 2016, now Pat. No. 11,234,949.

(30) Foreign Application Priority Data

May 14, 2015  (IT) ........................ 102015000015060

(51) Int. Cl.
| | |
|---|---|
| *A61K 31/198* | (2006.01) |
| *A61K 31/375* | (2006.01) |
| *A61K 31/405* | (2006.01) |
| *A61K 31/4172* | (2006.01) |
| *A61K 31/4415* | (2006.01) |
| *A61K 31/51* | (2006.01) |
| *A61P 1/04* | (2006.01) |
| *A61K 47/38* | (2006.01) |

(52) U.S. Cl.
CPC .......... *A61K 31/198* (2013.01); *A61K 31/375* (2013.01); *A61K 31/405* (2013.01); *A61K 31/4172* (2013.01); *A61K 31/4415* (2013.01); *A61K 31/51* (2013.01); *A61K 47/38* (2013.01); *A61P 1/04* (2018.01); *A61K 2300/00* (2013.01)

(58) Field of Classification Search
CPC .. A61K 31/198; A61K 31/375; A61K 31/405; A61K 31/4172; A61K 31/4415; A61K 31/51; A61K 47/38; A61P 1/04
See application file for complete search history.

(56) References Cited

U.S. PATENT DOCUMENTS

| | | | |
|---|---|---|---|
| 9,707,198 B2 * | 7/2017 | Giorgetti | .............. A61K 31/405 |
| 11,234,949 B2 | 2/2022 | Giorgetti | |
| 2022/0047539 A1 | 2/2022 | Giorgetti | |

FOREIGN PATENT DOCUMENTS

| | | |
|---|---|---|
| EP | 3294279 B1 | 1/2020 |
| WO | 2016/181335 A1 | 11/2016 |

OTHER PUBLICATIONS

Tsujimoto et al. Oncology Reports, 33, pp. 33-39, Jan. 2015 (published online Oct. 23, 2014). (Year: 2015).*
Office Action with Examination Search Report dated Jul. 19, 2022, issued in Canada Application No. 2,981,757, 3 pages.
Erickson, Rick, et al., "Effects of glutamine on head and neck squamous cell carcinoma", Otolaryngology—Head and Neck Surgery, vol. 121, No. 4, Oct. 1999, pp. 348-354.
Klimberg, V. Suzanne, et al., "Prophylactic Glutamine Protects the Intestinal Mucosa From Radiation Injury", Cancer, vol. 66, No. 1, Jul. 1, 1990, pp. 62-68.

* cited by examiner

*Primary Examiner* — Kara R McMillian
(74) *Attorney, Agent, or Firm* — Nixon & Vanderhye P.C.

(57) ABSTRACT

Amino acid composition for use in the treatment of mucositis in patients suffering from head and neck cancer, undergoing radiation therapy and/or chemotherapy, the composition comprising an active agent, the active agent comprising the amino acids: glutamine, leucine, isoleucine, valine, lysine, threonine, histidine, phenylalanine, methionine, tryptophan, tyrosine, and cystine, wherein the glutamine:leucine weight ratio is in the range 4.3 to 5.3.

11 Claims, No Drawings

COMPOSITIONS COMPRISING AMINO ACIDS FOR USE IN THE TREATMENT OF MUCOSITIDES IN NEOPLASIA PATIENTS UNDERGOING RADIATION THERAPY AND/OR CHEMOTHERAPY

CROSS-REFERENCE TO RELATED APPLICATIONS

This application is a continuation of U.S. patent application Ser. No. 15/571,130 filed on Nov. 1, 2017, which is the U.S. national phase of International Application No. PCT/IB2016/052724 filed on May 12, 2016, which designated the U.S. and claims priority to Italy Patent Application No. 102015000015060 filed on May 14, 2015, the entire contents of each of which are hereby incorporated by reference.

FIELD OF THE INVENTION

The present disclosure refers to compositions comprising amino acids for use in the treatment of mucositides in patients suffering from neoplasia, in particular neoplasia of the cervical-cephalic region, undergoing radiation therapy and/or chemotherapy.

BACKGROUND

In patients suffering from neoplasias of the cervical-cephalic region (also referred to as head and neck cancer), chemotherapy and radiation therapy have resulted in good control of tumour growth and improved survival rate. However, such patients are often subject to the development of severe mucositides over large areas of the oral cavity, pharynx and larynx, which are just induced by radiotherapeutic and/or chemotherapeutic treatments. Because of such mucositides, patients often become unable to consume oral medications, which involves, in some cases, the need to decrease the dose of chemotherapy or to stop radiation therapy with obviously negative results for the patient.

In order to overcome the problems caused by such mucositides induced by antitumor treatments, there have been put into effect various attempts to control and reduce the occurrence and/or severity of the same, such as, for example, more attention to oral care, and use of topical anesthetics and antimicrobials. However, to date, a therapy which concretely allows to counteract or at least to reduce the occurrence and/or severity of such mucositides in this class of patients has not yet been identified.

Glutamine is the most abundant amino acid in our body. It is a primary fuel, and an essential precursor for the nucleotide biosynthesis in rapidly proliferating cells such as enterocytes, fibroblasts, lymphocytes and macrophages, for which it represents an essential amino acid. Moreover, glutamine serves as a substrate for glutathione synthesis and has antioxidant properties.

If exposed to severe stress, the body is unable to synthesize sufficient amounts of this amino acid, resulting in decreased plasma levels of glutamine. In these conditions, the mucosal immune system is inhibited and the release of glutamine by muscle tissue is reduced.

It has been shown, moreover, that patients suffering from advanced head and neck cancer, undergoing cytotoxic therapy, develop glutamine deficiency (1). Over the last two decades, several studies have examined whether the glutamine reduced the incidence and severity of mucositis induced by radiation therapy and/or chemotherapy (2-7), however, without reaching a conclusion about the actual role of glutamine in the prevention or treatment of such mucositides (4-6). In the publication Jebb 1994 (6), the authors attest, in fact, that by administering 16 grams of glutamine per day significant results in the treatment/prevention of mucositis were not observed.

The results of a clinical, double-blind, randomized, placebo-controlled study on the efficacy of the administration of glutamine to patients suffering from head and neck cancer (8) were recently published and concluded that glutamine—when given in a daily dose of 30 g—significantly decreases the severity of mucositis induced by antitumor treatments. In this publication, it is also stated that concentrations of glutamine between 10 and 26 grams/day are ineffective for the treatment of mucositis. The hematochemical data of patients subject of the study (8) demonstrate, however, a worsening of several parameters compared to the control group. In particular, there get worse total neutrophil count and total leukocyte count, hemoglobin, creatine phosphokinase, as well as iron and zinc, which implies, in these patients, the occurrence of a greater appearance of local and systemic bacterial infections, asthenia at rest and fatigue during motor activity resulting in increased cardio-respiratory work, reduced ability to produce muscle energy, decreased multidistrict antioxidative capacity. Finally, these situations cause, especially in the elderly, impaired cognitive function. In summary, a negative state of these parameters makes the patient much more "fragile".

SUMMARY OF THE INVENTION

The present disclosure has the purpose of providing amino acid based compositions for use in the treatment of mucositides in patients suffering from neoplasia of the cervical-cephalic region, undergoing radiation therapy and/or chemotherapy, which allow to reduce the occurrence and/or severity of mucositides and, at the same time, to counteract the oxidative stress and the inhibition of the mucosal immune system caused by antineoplastic treatment.

According to the present disclosure, the above purpose is achieved thanks to the object specifically indicated in the claims that follow, which are intended as an integral part of the present disclosure.

One embodiment of the present disclosure relates to a amino acid composition for use in the treatment of mucositides in patients suffering from neoplasia of the cervical-cephalic region, undergoing radiation therapy and/or chemotherapy, comprising an active agent, wherein the active agent comprises the amino acids: glutamine, leucine, isoleucine, valine, lysine, threonine, histidine, phenylalanine, methionine, tryptophan, tyrosine and cystine, wherein the glutamine:leucine weight ratio is comprised in the range 4.3 to 5.3.

The Inventor has found that the compositions herein described are able to determine i) a reduction of occurrence and/or severity of mucositis induced by antineoplastic treatment, ii) an improvement of the immunohaematological framework compared to controls and iii) a reduction of occurrence and/or severity of dysphagia caused by neoplasia itself or by antineoplastic treatment, thanks to an antiinflammatory effect of the composition which allows to counteract the onset of anorexia, "fatigue" and/or sarcopenia, and further iv) an improvement of cell metabolism by preventing a ipercatabolic condition prevalence.

An advantage related to the use of the compositions herein described resides in the high tolerability of the compositions that may be administered to these patients even when suffering from dysphagia.

Another advantage linked to the use of the composition described herein lies in the fact that the use of amino acids in free form comprised in the active agent allows producing such compositions at a comparatively extremely low cost with respect to synthetic proteins and growth factors, through per se known production processes and widely used in the field of preparing compositions based on free amino acids. The field of application of the invention may however also be extended to amino acids obtained through genetic engineering or any other artificial method.

DETAILED DESCRIPTION OF PREFERRED EMBODIMENTS

In the following specification, numerous specific details are given to provide a thorough understanding of the embodiments. The embodiments may be implemented without one or more of the specific details, or with other methods, components, materials, etc. In other instances, well-known features, materials or operations are not shown or described in detail to avoid obscuring aspects of the embodiments.

The reference throughout this specification to "one embodiment" or "an embodiment" means that a particular feature, structure or characteristic described in connection with the embodiment is included in at least one embodiment. Thus, the phrase appearances "in one embodiment" or "in an embodiment" in various places throughout this specification do not necessarily all refer to the same embodiment. Additionally, the particular features, structures or characteristics may be combined in any suitable manner in one or more embodiments. The headings provided herein are for convenience only and do not interpret the scope or purpose of the embodiments.

In one embodiment of the present disclosure, the amino acid composition for use in the treatment of mucositides in patients suffering from neoplasia of the cervical-cephalic region, undergoing radiation therapy and/or chemotherapy, comprises an active agent, wherein the active agent comprises the amino acids: glutamine, leucine, isoleucine, valine, lysine, threonine, histidine, phenylalanine, methionine, tryptophan, tyrosine, and cystine, wherein the glutamine:leucine weight ratio is comprised in the range 4.3 to 5.3, preferably 4.5 to 5.0, more preferably is 4.5.

Frequently, patients suffering from neoplasia of the cervical-cephalic region, within 4-5 weeks from the beginning of radiochemotherapy, develop mucositis, dermatitis and soft tissue swelling. These side effects are due to the production of reactive oxygen species (ROS) and proinflammatory cytokines (IL-1, IL-6, TNF-$\alpha$) whose synthesis is stimulated by activation of transcription factors, in particular the nuclear factor-$\kappa$B (NF-$\kappa$B).

Clinically, the patient experiences pain, production of thick mucus, dry mouth (xerostomia), tissue tumefaction often accompanied by acute dysphagia. It follows malnutrition or even a deterioration of the same, this being present in about 30-50% of cases already at the time of diagnosis. Among the causes of pre-treating malnutrition can be recognized odynophagia, mechanical obstruction, dysphagia due to tumor infiltration and, last but not least, factors such as anorexia and "fatigue", secondary to direct and indirect tumor production of proinflammatory cytokines (IL-1, IL-6, TNF).

In addition, it is reasonable to assume that sarcopenia that characterizes the malnourished patient can also affect the muscles involved in the swallowing process and thus result in the onset or even worsening of dysphagia (if pre-existing). It therefore creates a vicious circle of malnutrition and dysphagia.

In the most of patients in the 3 months following the start of the antitumor treatment, the acute effects are resolved and swallowing begins to improve.

However, in some patients, the acute inflammation can be so prolonged or exuberant that during the process of tissue repair induced by antitumor therapy the fibrotic phase prevails over the regenerative phase. It follows tissue fibrosis, lymphedema and, consequently, late dysphagia (even years later).

Experimental and clinical studies have shown that glutamine (9) i) is an essential precursor (via glutamate) of the synthesis of intracellular glutathione (GSH) (tripeptide with cell protective action against oxidative stress), and ii) is able to directly and indirectly protect (through the expression of Heat Shock Proteins) the cell from damage induced by proinflammatory cytokines (antiinflammatory action).

Clinical studies conducted by administering the composition of the present disclosure to patients suffering from neoplasia of the cervical-cephalic region and undergoing radiation therapy and/or chemotherapy, have shown that the composition is capable of improving the physical condition of patients, by determining i) a reduced occurrence and/or severity of mucositis induced by antineoplastic treatment, ii) an unexpected improvement in immunohaematological framework compared with untreated patients, and iii) a reduction of occurrence and/or severity of dysphagia caused by neoplasia itself or by antineoplastic treatment, thanks to an antiinflammatory effect of the composition which allows to counteract the onset of anorexia, "fatigue" and/or sarcopenia, and further iv) an improvement of cell metabolism in these patients by preventing an ipercatabolic condition prevalence.

The experimental data obtained in the clinical study conducted with the composition herein described show that the administration of the composition—in patients suffering from head and neck cancer and undergoing antineoplastic treatment—for 6 weeks (21 g of glutamine and 15 g of essential amino acids/day) reduces the mucositis more than what it has been shown in the prior art (8) and, at the same time, allows to counteract oxidative stress (thanks to the antiinflammatory action exerted by the composition) and the inhibition of the immune system of the mucosae caused by antineoplastic treatment and to improve the cellular metabolism (by preventing the onset of hypercatabolism), by determining the maintenance of physiological levels of blood albumin and several significant parameters of the immunohaematological framework.

In the patients of the control group it was, in fact, observed significantly more frequent mucositis and asthenia at rest and fatigue during motor activity resulting in increased cardio-respiratory work, reduced capability to produce muscle energy, reduced multidistrict antioxidative capacity, worsening of chronic inflammatory state that is revealed with lymphedema and late dysphagia, as well as with less compensated haematological framework.

The experimental data show that, in patients treated with the composition herein disclosed, the maintenance of levels of albumin, muscle strength and a reduction in the frequency of mucositis and dysphagia were obtained.

In a completely unexpected way, the Inventor of the present composition, in fact, has demonstrated that the administration of 20-25 g/day of glutamine supplemented with 15-20 g/day of essential amino acids (i.e. leucine, isoleucine, valine, lysine, threonine, histidine, phenylalanine, methionine, tryptophan, tyrosine, and cystine) allows an use of glutamine in various body areas, especially in immunocompetent cells and tissues, more than it can be derived only by exogenous glutamine. In addition, the composition allows to maintain (not shown in the prior art as indicated for example in the publications (8) and (10)) unaltered levels of hemoglobin, albumin, total neutrophils and leukocytes.

The composition object of the present disclosure allows, in fact, to enhance multidistrict protein syntheses in the presence of a systemic and regional inflammatory state in existence of hypercatabolism, which is then contrasted and brought back to a cell physiological metabolic state. Counteracting the hypercatabolism allows, in fact, to preserve the integrity of tissues, stimulate the reparative processes and preserve the proper functioning of the immune system, mainly to oral mucosa level.

In a preferred embodiment, the composition of the present disclosure has a composition (expressed as a single dose, 12 mg sachet of total amino acids) as shown in the following Table 1.

TABLE 1

| Ingredient | Amount by weight mg/sachet | % w/w based on total | Range % w/w | Preferred range % w/w |
| --- | --- | --- | --- | --- |
| L-Glutamine | 7000.00 | 58.33 | 50-65 | 55-60 |
| L-Leucine | 1562.50 | 13.02 | 10-15 | 12-14 |
| L-Isoleucine | 781.25 | 6.51 | 4-8 | 5-7 |
| L-Valine | 781.25 | 6.51 | 4-8 | 5-7 |
| L-Lysine | 812.50 | 6.77 | 4-8 | 5-7 |
| L-Threonine | 437.50 | 3.64 | 2.5-5 | 3-4 |
| L-Histidine | 187.50 | 1.56 | 0.5-2.5 | 1-2 |
| L-Phenylalanine | 125.00 | 1.04 | 0.5-2.5 | 0.5-1.5 |
| L-Methionine | 62.50 | 0.52 | 0.3-0.7 | 0.4-0.6 |
| L-Tryptophan | 25.00 | 0.21 | 0.1-0.4 | 0.1-0.3 |
| L-Tyrosine | 37.50 | 0.31 | 0.1-0.5 | 0.2-0.4 |
| L-Cystine | 187.50 | 1.56 | 05.-2.5 | 1-2 |
| Total weight | 12000.00 | 100% | | |

The present composition may also comprise, in preferred embodiments, thickening agents that—originating a composition in gel form—allow the composition intake by patients suffering from dysphagia caused by neoplasia itself or late onset of the same due to the non-physiological metabolic state.

The thickening agents that can be added to the amino acid composition described herein, can be selected in the group consisting of xanthan gum, methylhydroxypropylcellulose, konjac gum, konjak glucomannan, arabic gum (acacia gum), modified starches. Preferably, the one or more thickening agents are present in an amount between 2% and 30% by weight, preferably between 4% and 15% by weight, with respect to the active agent weight.

The presence of one or more of such thickening agents allows to thicken the liquid, preferably water, wherein the composition is dispersed before consumption, giving rise to a composition with an ideal viscosity for the ingestion by a patient suffering from dysphagia.

It is known that people suffering from dysphagia generally lack of proper muscle coordination and control to properly close the trachea or do not have the ability to properly push down the entire alimentary bolus and/or beverage to the stomach. It is therefore extremely important that foods consumed by dysphagic patients have the right viscosity and consistency.

The amount of liquid to add to the composition described herein will depend, for example, on the consistency to be obtained. This parameter will be evaluated and determined by a skilled person, taking into account also the degree of dysphagia of the patient.

In some embodiments, the composition described herein further comprises vitamins, preferably selected from vitamin B1, vitamin B6 and vitamin C.

In a further embodiment, the composition also includes carbohydrates, additives and/or flavourings.

Preferred carbohydrates can be chosen from various types of maltodextrins. The additive may be selected from tribasic sodium citrate dehydrated, aspartame powder, acesulfame potassium, sucralose. A preferred flavouring is banana flavour.

According to some embodiments of the present disclosure, the preferred isoleucine:leucine weight ratio ranges from 0.20 to 0.70, preferably from 0.40 to 0.60 and/or the valine:leucine weight ratio ranges from 0.20 to 0.80, preferably from 0.40 to 0.70.

In a further embodiment, the threonine:leucine weight ratio ranges from 0.15 to 0.50, preferably from 0.20 and 0.45 and/or the lysine:leucine weight ratio ranges from 0.15 to 0.60, preferably from 0.30 to 0.55.

In another embodiment, the leucine:isoleucine:valine weight ratio is equivalent to 2:1:1.

In a further embodiment, assuming that the sum of leucine, isoleucine, valine, threonine and lysine is 1, the overall amount of the further essential amino acids can further range from 0.02 to 0.25 (i.e. 1:0.02-0.25), preferably from 0.05 to 0.15 (i.e. 1:0.05-0.15), still intended as weight ratio.

In a further embodiment, cystine is present in a weight amount comprised between 150% and 350% of methionine.

In some embodiments, tyrosine is present in the composition in an amount comprised between 15 and 50%, preferably between 20 and 35%, of the weight amount of phenylalanine.

In a further embodiment, the active agent consists of the amino acids: glutamine, leucine, isoleucine, valine, lysine, threonine, histidine, phenylalanine, methionine, tryptophan, tyrosine and cystine, wherein the glutamine:leucine ratio is between 4.3 and 5.3, preferably between 4.5 and 5.0, more preferably is 4.5.

In one or more embodiments, as shown in Table 1 and in the following Table 2, the amino acids included in the composition consist exclusively of the amino acids of the active agent i.e. glutamine, leucine, isoleucine, valine, lysine, threonine, histidine, phenylalanine, methionine, tryptophan, tyrosine and cystine; the composition is free of any other further different amino acids.

In one or more embodiments, glutamine is present in an amount between 50 and 65%, preferably between 55 and 60% by weight with respect to the total weight of the active agent.

Furthermore, in particular, when preparing the compositions according to the instant disclosure, and specifically the active agent, the amino acids serine, proline, glycine, alanine, glutamic acid and, above all, arginine are preferably avoided, given that they can be counterproductive or even harmful in some concentrations or stoichiometric ratios with the said formulation.

The above mentioned amino acids can be replaced with their respective pharmaceutically acceptable derivatives, that is salts.

Preferably, the composition is in the form of a dry powder and, in order to be administered to the patient it is dispersed in a liquid, preferably water. Further specifications, in terms of quantity and ratios between the various amino acids provided by the compositions for use in the treatment herein disclosed, are contained in the appended claims, which form an integral part of the technical teaching provided herein in relation to invention.

The results provided herein show that thanks to the composition herein disclosed it is possible to obtain:
- a significant reduction of grade 3 mucositis (25% vs 55%) ($p<0.05$);
- a late onset of grade 3 mucositis (23.3±3.6 days vs 38.5±4.9 days) ($p<0.001$);
- a better blood framework, wherein the levels of albumin, total neutrophil count, total leukocyte count and haemoglobin are maintained unaltered;
- a maintenance of muscle strength (measured with a hand-grip) at the end of treatment (+0.4 kg vs −7 kg) ($p<0.05$). This finding is significant with respect to the prevention of generalized sarcopenia and it is suggestive, for the correlation between muscle strength and swallowing, of a possible minor dysphagia;
- a trend (p 0.056) toward less perceived fatigue, assessed by FACT-HNSI scale.

Materials and Methods

Patients

Patients with oropharyngeal neoplasia, candidates for radiation therapy (RT) or radiochemotherapy (RCT). Exclusion criteria: severe weight loss (>5% in 1 month or >10% in 6 months), inadequate ingesta (<60% of requirements), severe dysphagia, kidney failure, liver failure, palliative radiation therapy.

Study Design

Blind pilot study, with randomization in 2 groups, using automatically generated numerical sequence: study group (G, 20 patients) and control group (C, 20 patients). In the study group the composition herein disclosed was orally administered in gel form, in the amount of 3 sachets/day, far from meals, from 7 days before the start of treatment (T −1) and up to completion of the same (6 weeks).

Patients were subjected to the following regimen of radiation therapy with intensity-modulated beams (IMRT): total dose of radiation 66-70 Gy (1 session/day for 5 days/week). Associated chemotherapy (15 patients in the study group and 15 patients in the control group) included: cisplatin i.v. 40 mg/m$^2$ (weekly) or 100 mg/m$^2$ (every three weeks).

The following primary endpoints were evaluated: incidence, severity and onset timing of mucositis. As secondary endpoints there were considered: mucositis-related symptoms, life quality, nutritional status, muscle strength, need for oral integration/artificial nutrition, discontinuation of treatment.

In both groups it was used, in combination with RT or RCT, the same protocol of prevention/treatment of mucositis (as required).

All patients were subjected at T-1 and then, weekly, (T0-T6) to a medical examination and dietetic counseling. At each meeting, there were carried out the following evaluations: presence of mucositis-related symptoms (PROMS scale), life quality (FACT/HNSI NCCN scale), nutritional status (weight, blood sampling for tests, ingesta per os through food diaries of the past 3 days), muscle strength using hand-grip (averaged over three determinations with Jamar dynamometer).

The energy requirement has been set in 30 kcal/kg/day, the protein requirement has been set in 1.5 g/kg/day.

In patients with inadequate intakes there have been used oral supplements (ingesta≥60% of requirements) or NA (ingesta<60% of requirements).

The assessment of the severity and onset timing of mucositis was carried out on a weekly basis, by a radiotherapist, using the WHO scale.

Statistic Analysis

Student's t test, Chi Square, Fischer test, Kaplan-Meier curve.

The Composition

The study group (group G) received the composition herein disclosed that provided 36 g of amino acids/day (12 g three times a day diluted in half a glass of water until the discharge of the patient).

The amount of each amino acid contained in the single dose of the composition administered to patients is provided in Table 2.

TABLE 2

| Ingredient | mg/sachet |
|---|---|
| L-Glutamine (146)* | 7000.00 |
| L-Leucine (131.17)* | 1562.50 |
| L-Isoleucine (131.17)* | 781.25 |
| L-Valine (117.15)* | 781.25 |
| L-Lysine (146.19)* | 812.50 |
| L-Threonine (119.12)* | 437.50 |
| L-Histidine (155.16)* | 187.50 |
| L-Phenylalanine (165.19)* | 125.00 |
| L-Methionine (149.21)* | 62.50 |
| L-Tryptophan (204.23)* | 25.00 |
| L-Tyrosine (181.19)* | 37.50 |
| L-Cystine (240.30)* | 187.50 |
| Total weight | 12000.00 |

*Molecular weight by "Amino Acid, Nucleic Acids & Related Compounds - Specification/General Tests", 8$^{th}$ Edition, Kyowa Hakko Kogyo Co., Ltd.

As can be seen from Table 2, the glutamine:leucine weight ratio is preferably 4.5:1; the weight ratio between leucine, isoleucine and valine is preferably equivalent to 2:1:1. The Table 1 also shows that the individual amounts of histidine, phenylalanine, methionine and tryptophan are preferably decreasing (that is, the amount of histidine is greater than that of phenylalanine, which is greater than that of methionine, which is greater than that of tryptophan) and the amount (weight in grams or moles) of cystine is preferably greater than that of tyrosine. The composition does not contain any other amino acids in addition to glutamine, leucine, isoleucine, valine, lysine, threonine, histidine, phenylalanine, methionine, tryptophan, tyrosine and cystine.

The amino acid composition also preferably includes carbohydrates, vitamins, flavourings and other pharmaceutically acceptable excipients, as well as in some cases thickening agents to allow the administration of the composition to dysphagic patients.

In Table 3 there are provided further examples of different variants (A, B and C) of the composition object of the present disclosure. The compositions designated A, B and C contain, in fact—in addition to the amino acids indicated in table 1—other additives in various qualitative and quantitative combinations, such as carbohydrates, vitamins, flavouring agents and thickening agents.

TABLE 3

| Ingredients | A | B | C |
|---|---|---|---|
| | | mg/sachet | |
| Maltodextrins | 11480.07 | 12514.80 | 10294.77 |

TABLE 3-continued

| Ingredients | A | B | C |
|---|---|---|---|
| | | mg/sachet | |
| L-glutamine | 7000.00 | 7000.00 | 7000.00 |
| L-leucine | 1562.50 | 1562.50 | 1562.50 |
| Xanthan gum | — | — | 1100.00 |
| L-lysine | 812.50 | 812.50 | 812.50 |
| Citric acid | 800.00 | — | 600.00 |
| L-isoleucine | 781.25 | 781.25 | 781.25 |
| L-valine | 781.25 | 781.25 | 781.25 |
| L-threonine | 437.50 | 437.50 | 437.50 |
| Sucrester | 200.00 | 200.00 | — |
| Lemon flavour | 200.00 | — | 200.00 |
| L-cystine | 187.50 | 187.50 | 187.50 |
| L-histidine | 187.50 | 187.50 | 187.50 |
| L-phenylalanine | 125.00 | 125.00 | 125.00 |
| L-methionine | 62.50 | 62.50 | 62.50 |
| Hydroxypropylcellulose | — | 60.00 | 500.00 |
| Aspartame | 40.00 | — | 48.00 |
| L-tyrosina | 37.50 | 37.50 | 37.50 |
| Polyvinylpyrrolidone | 34.70 | — | — |
| L-tryptophan | 25.00 | 25.00 | 25.00 |
| Acesulfame k | 20.00 | — | 28.00 |
| L-ascorbic ac. - vit. C | 15.385 | 15.385 | 15.38 |
| Beta carotene 1% | | | 4.00 |
| Tyamine hydrochloride - vit. B1 | 0.194 | 0.194 | 0.194 |
| Pyridoxine hydrochloride - vit. B6 | 0.182 | 0.182 | 0.182 |
| Total weight mg | 25000 | 25000 | 25000 |

First, the compositions shown in Table 3 are prepared by loading, in a four-way mixer, L-phenylalanine, L-tyrosine, L-tryptophan, vitamin B1 and vitamin B6 with L-Lysine, in order to obtain a pre-mix. The composition in % of the pre-mix is shown in following Table 4.

TABLE 4

| Ingredients | % |
|---|---|
| Maltodextrins | 83.296 |
| L-Phenylalanine | 8.333 |
| L-Methionine | 4.167 |
| L-Tyrosine | 2.500 |
| L-Tryptophan | 1.667 |
| Vitamin B1 | 0.019 |
| Vitamin B6 | 0.018 |

The ingredients are mixed for a period of 10 minutes to obtain a homogenous pre-mix.

The remainder of the ingredients listed in Table 3 are loaded in the four-way mixer and mixed for a period of 20 minutes to obtain a homogeneous final composition.

The composition object of the present disclosure is added and dispersed in a liquid, preferably water. The amount of liquid to add to the composition described herein depends, for example, on the consistency to be obtained. This parameter is evaluated and determined by a person skilled in the field also taking into account the degree of dysphagia of the patient.

Results

The administration of the composition herein described to the group of study patients allowed to obtain a significant reduction of grade 3 mucositis (25% vs 55% of controls) and a late onset of grade 3 mucositis (23.3±3.6 days vs 38.5±4.9 days of the control group), as shown by the data reported in Table 5.

TABLE 5

| | No. patients of study group | | No. patients of control group | |
|---|---|---|---|---|
| Mucositis level | Start of treatment | End of treatment | Start of treatment | End of treatment |
| 0 | 20 | 2 | 20 | 0 |
| 1 | 0 | 9 | 0 | 4 |
| 2 | 0 | 4 | 0 | 5 |
| 3 | 0 | 5 | 0 | 11 |

In addition, a preservation of muscle strength (measured by hand grip) at the end of treatment (+0.4 kg vs −7.0 kg in the control group) was observed. This finding is significant with respect to the prevention of generalized sarcopenia and for the correlation between muscle strength and swallowing capacity, with a consequent dysphagia reduction of patients in the study group.

Also the tendency towards asthenia (assessed by FACT-HNSI scale—$p=0.056$) is significantly reduced in patients in the study group compared with patients in the control group.

The composition object of the present disclosure allows, in fact, to enhance multidistrict protein syntheses in the presence of a systemic and regional inflammatory state in the occurrence of hypercatabolism, which is then counteracted and brought back to a cell physiological metabolic state, considering the severe radiochemotherapeutic intervention to which the patients of the study group are subjected. The composition is able to counteract the hypercatabolism and then to maintain the tissue integrity, stimulate the reparative processes and preserve the proper functioning of the immune system, mainly to oral mucosa level.

Clinical data, below, show a general maintenance of the most important blood parameters related to catabolism, as is evident from the data shown in Table 6.

TABLE 6

| | Patients of study group | | Patients of control group | |
|---|---|---|---|---|
| | Start of treatment | End of treatment | Start of treatment | End of treatment |
| Neutrophil count (×1000/mmc) | 4.237 ± 0.98 | 4.034 ± 0.872 | 4.339 ± 1.028 | 3.736 ± 1.236 |
| Leukocyte count (×1000/mmc) | 1.520 ± 0.623 | 1.147 ± 0.732 | 1.481 ± 0.754 | 0.902 ± 0.812 |
| Hemoglobin (g/dl) | 12.67 ± 1.34 | 11.93 ± 1.76 | 12.51 ± 1.73 | 10.47 ± 1.98 |
| PCR (mg/dl) | 0.34 ± 0.6 | 0.32 ± 0.57 | 0.40 ± 0.65 | 0.43 ± 0.69 |
| Albumin (g/dl) | 4.49 ± 0.3 | 4.27 ± 0.45 | 4.38 ± 0.39 | 3.87 ± 0.49 |
| Hand grip (kg)* | 35.05 ± 16.96 | 35.47 ± 14.12 | 37.12 ± 14.0 | 30.18 ± 13.76 |
| Weight (kg) | 69.9 ± 20.9 | 66.3 ± 19.8 | 71.5 ± 18.9 | 66.4 ± 17.0 |

*$p < 0.05$

In particular, total neutrophils, total leukocytes, hemoglobin and albumin, contrary to what reported in Tsujimoto et al. (8) with a dosage of 30 grams of glutamine alone, are maintained in an almost physiological level and do not decrease over time as observed in patients of the control group.

In particular, it is evident that the present composition allows to obtain unexpected results compared to the data provided in (8) wherein during the study period, the treated group showed worse immunohaematological analytical data compared to placebo. In (8), in treated patients there is a reduction of levels of total neutrophil count, total leukocyte count, hemoglobin, while there is an increase of the levels of creatine phosphokinase (CPK), wherein a CPK level that grows over time is related to cellular synthesis damage and reduced use of energy-ATP.

The experimental data provided herein demonstrate that patients receiving the composition of the present disclosure will not be subject to frequent local and systemic bacterial infections, and will present less frequent asthenia and fatigue at rest during motor activity. Patients in the study group maintain, in fact, the ability to produce muscle energy.

In summary, the maintenance of the physiological levels of the above parameters allows the patient to be more tonic and less subject to fatigue during the motor activity, with good management of the cardio-respiratory work, maintaining the ability to produce muscle energy, and the multidistrict antioxidative capacity. Finally, especially in elderly, no impairment of the cognitive functions has been observed.

REFERENCES

1. Savarese et al.: Prevention of chemotherapy and radiation toxicity with glutamine *Cancer Treat Rev* 29: 501-513, 2003.
2. Huang et al.: Oral glutamine to alleviate radiation-induced oral mucositis: a pilot randomized trial. *Int J Radiat Oncol Biol Phys* 46: 535-539, 2000.
3. Skubitz K M and Anderson P M: Oral glutamine to prevent chemotherapy induced stomatitis: a pilot study. *J Lab Clin Med* 127: 223-228, 1996.
4. Jebb et al.: A pilot study of oral glutamine supplementation in patients receiving bone marrow transplants. *Clin Nutr* 14: 162-165, 1995.
5. van Zaanen et al.: Parenteral glutamine dipeptide supplementation does not ameliorate chemotherapy-induced toxicity. *Cancer* 74: 2879-2884, 1994.
6. Jebb et al: 5-fluorouracil and folinic acid-induced mucositis: no effect of oral glutamine supplementation. *Br J Cancer* 70: 732-735, 1994.
7. Anderson et al.: Oral glutamine reduces the duration and severity of stomatitis after cytotoxic cancer chemotherapy. *Cancer* 83: 1433-1439, 1998.
8. Tsujimoto et al.: L-glutamine decreases the severity of mucositis induced by chemoradiation therapy in patients with locally advanced head and neck cancer: a double-blind, randomized, placebo-controlled trial. *Oncology Reports* 33:33-39, 2015.
9. Kuhn K S et al.: Glutamine as indispensable nutrient in oncology: experimental and clinical evidence. *Eur. J. Nutr.;* 49 (4):197-210, 2009
10. Samocha-Bonet et al.: Glycemic effects and safety of L-Glutamine supplementation with or without sitagliptin in type 2 diabetes patients-a randomized study. *PLoS One* 9 (11): 1-7, 2014

The invention claimed is:

1. A method of treating mucositis in a patient who is suffering from neoplasia of the cervical-cephalic region and who is undergoing radiation therapy and/or chemoradiotherapy, the method consists of:
   (1) selecting an amino acid composition for use in the treatment of mucositis in the patient who is suffering from neoplasia of the cervical-cephalic region and who is undergoing radiation therapy and/or chemoradiotherapy, the amino acid composition consists of:
      (i) an active agent, said active agent consists of the amino acids glutamine, leucine, isoleucine, valine, lysine, threonine, histidine, phenylalanine, methionine, tryptophan, tyrosine, and cystine, wherein
         (a) the amino acid composition is free of any further different amino acids,
         (b) the glutamine:leucine weight ratio is in the range 4.3 to 5.3, and
         (c) glutamine is present in an amount between 50 and 65% by weight with respect to the total weight of the active agent, and
      (ii) optionally at least one of, none of which have any amino acids: carbohydrates, at least one thickening agent, at least one vitamin, pharmaceutically acceptable excipients, and flavouring substances, and
   (2) administering the amino acid composition to the patient to treat mucositis in the patient who is suffering from neoplasia of the cervical-cephalic region and who is undergoing radiation therapy and/or chemoradiotherapy.

2. The method according to claim 1, wherein the leucine:isoleucine:valine weight ratio is equivalent to 2:1:1.

3. The method according to claim 1, wherein
the isoleucine:leucine weight ratio is in the range 0.2-0.7, and/or
the valine:leucine weight ratio range is in the range 0.2-0.8.

4. The method according to claim 1, wherein
the threonine:leucine weight ratio is in the range 0.15-0.50, and/or
the lysine:leucine weight ratio is in the range 0.15-0.60.

5. The method according to claim 1, wherein the at least one thickening agent is selected from the group consisting of xanthan gum, cellulose and derivatives thereof, konjak gum, konjak glucomannan, Arabic gum, modified starches.

6. The method according to claim 1, wherein the at least one vitamin is selected from vitamin $B_1$, vitamin $B_6$, vitamin C.

7. The method according to claim 1, wherein the glutamine is present in an amount between 55 and 60% by weight with respect to the total weight of the active agent.

8. The method according to claim 3, wherein the isoleucine:leucine weight ratio is between 0.4-0.6.

9. The method according to claim 3, wherein the valine:leucine weight ratio range is between 0.4-0.7.

10. The method according to claim 4, wherein the threonine:leucine weight ratio is between 0.20-0.45.

11. The method according to claim 4, wherein the lysine:leucine weight ratio is between 0.30-0.55.

* * * * *